(12) United States Patent
Keays et al.

(10) Patent No.: US 12,702,324 B2
(45) Date of Patent: Aug. 11, 2026

(54) SOBRIETY MONITORING SYSTEMS AND FEATURES RELATED THERETO

(71) Applicant: Soberlink Healthcare LLC, Huntington Beach, CA (US)

(72) Inventors: Brad Keays, Manhattan Beach, CA (US); Daniel Rhodes, San Jose, CA (US); Casey Hanrahan, Fullerton, CA (US); Christopher J. Pursley, Fullerton, CA (US)

(73) Assignee: Soberlink Healthcare LLC, Huntington Beach, CA (US)

( * ) Notice: Subject to any disclaimer, the term of this patent is extended or adjusted under 35 U.S.C. 154(b) by 368 days.

(21) Appl. No.: 18/435,690

(22) Filed: Feb. 7, 2024

(65) Prior Publication Data

US 2024/0306937 A1 Sep. 19, 2024

Related U.S. Application Data

(60) Provisional application No. 63/444,146, filed on Feb. 8, 2023.

(51) Int. Cl.

| | |
|---|---|
| ***A61B 5/097*** | (2006.01) |
| ***A61B 5/00*** | (2006.01) |
| ***A61B 5/08*** | (2006.01) |
| ***F03G 7/06*** | (2006.01) |
| ***F04B 43/04*** | (2006.01) |
| ***F04B 45/027*** | (2006.01) |

(Continued)

(52) U.S. Cl.
CPC ............ *A61B 5/097* (2013.01); *A61B 5/0002* (2013.01); *A61B 5/082* (2013.01); *A61B 5/4845* (2013.01); *F03G 7/0614* (2021.08); *F04B 45/027* (2013.01); *G01N 2001/241* (2013.01); *G01N 33/497* (2013.01)

(58) Field of Classification Search
CPC ..... F04B 45/027; A61B 5/097; G01N 33/497; G01N 33/4972; G01N 33/4975; G01N 33/4977; G01N 2001/241; F03G 7/0614; F03G 7/06143; F03G 7/06145; F03G 7/065
See application file for complete search history.

(56) References Cited

U.S. PATENT DOCUMENTS 4,945,727 A * 8/1990 Whitehead .......... F03G 7/06143 60/527
5,622,482 A * 4/1997 Lee ......................... F04B 17/00 417/415

(Continued)

FOREIGN PATENT DOCUMENTS

JP 2006037786 A * 2/2006

*Primary Examiner* — Herbert K Roberts
(74) *Attorney, Agent, or Firm* — ONE LLP

(57) ABSTRACT

Systems, methods and devices are disclosed for monitoring sobriety using a hand-held breath testing device. The hand-held breath testing device comprises a sample pump which utilizes a bellows assembly to draw an air sample through an inlet port and into the sample pump. The sample pump comprises a bi-stable spring and nitinol-based structures which cause the pump to actuate and allow the bellows to expand and compress. The sample pump can be utilized with other sampling devices, including but not limited to medical devices, wherein a sampling of a measured volume of gas is desired.

20 Claims, 9 Drawing Sheets

(51) Int. Cl.
*G01N 1/24* (2006.01)
*G01N 33/497* (2006.01)

(56) References Cited

U.S. PATENT DOCUMENTS

| | | | | | |
|---|---|---|---|---|---|
| 6,059,546 | A * | 5/2000 | Brenan | F03G 7/0646 | 417/393 |
| 7,052,251 | B2 * | 5/2006 | Nason | F04B 19/006 | 604/152 |
| 8,584,456 | B1 * | 11/2013 | McKnight | H02N 10/00 | 60/527 |
| 9,744,563 | B2 * | 8/2017 | Benjamin | B06B 3/02 | |
| 2003/0127090 | A1 * | 7/2003 | Gifford | A61M 16/0057 | 623/23.65 |
| 2004/0068985 | A1 * | 4/2004 | Mernoe | A61M 5/142 | 60/527 |
| 2004/0078028 | A1 * | 4/2004 | Flaherty | A61M 5/1452 | 604/892.1 |
| 2012/0151913 | A1 * | 6/2012 | Foshansky | F03G 7/06143 | 60/527 |
| 2012/0209187 | A1 * | 8/2012 | Kamen | A61M 5/14248 | 604/131 |
| 2015/0048921 | A1 * | 2/2015 | Alacqua | H01H 61/0107 | 337/140 |
| 2017/0303819 | A1 * | 10/2017 | Nothacker | G08B 21/18 | |
| 2019/0203701 | A1 * | 7/2019 | Motzki | G05G 5/06 | |
| 2022/0205434 | A1 * | 6/2022 | Citro | F03G 7/0614 | |

* cited by examiner

SOBRIETY MONITORING SYSTEMS AND FEATURES RELATED THERETO

CROSS-REFERENCE TO RELATED APPLICATIONS

The present application claims priority to U.S. Provisional Patent Application No. 63/444,146, filed Feb. 8, 2023, the entirety of which is incorporated by reference herein.

FIELD OF THE INVENTION

This disclosure relates generally to systems, device and methods for remote sobriety monitoring. In particular, this disclosure relates to a sample pump that can be utilized with a hand-held breath testing device.

BACKGROUND OF THE INVENTION

Recovering alcoholics or other substance abusers may benefit from the supervision of a sober chaperone such as a sober buddy, sober companion or sober coach to assist a recovering alcoholic in maintaining abstinence from alcohol outside of a treatment facility. Such a sober companion commonly chaperones the recovering alcoholic or substance abuser on a constant basis, or may be available on an on-call basis to accompany a recovering alcoholic or substance abuser periodically or as needed during certain activities. Such supervisory care can be quite expensive, which may have the unfortunate consequence of reducing or eliminating the services of such supervisory care.

People struggling with alcohol often conceal their abuse, making it difficult for concerned family members to confirm their suspicions and intervene. Because alcohol leaves the system quickly, it is important to test for alcohol consumption by using a breathalyzer or another similar alcohol testing method. Confirmation of a drinking problem becomes increasingly difficult during periods when testing for alcohol consumption is not easily enforced, such as during travel for business or college, for example. It would be useful to provide a method for parents to be able to monitor alcohol use anywhere by their children, and for spouses to monitor alcohol use anywhere by their spouses, in order to eliminate suspicions and confirm whether the family member has a drinking problem. It would also be useful to provide a method for companies to deter alcohol abuse by employees during work hours. Industries that rely heavily on driving and have limited employee supervision could also benefit from a method allowing the monitoring of alcohol use by employees as a way to confirm employee sobriety during work hours. Although drug testing is common in the workplace, since alcohol is metabolized relatively quickly, and is not easily tested, it would also be useful to provide a method for immediate confirmation of an employee's alcohol level at any given time.

Court ordered sobriety is also commonly required as a condition of probation or other court imposed rehabilitative or behavior altering programs. Reporting to a stationary facility, one's probation officer, or even one's home in order to be tested for substance use is often an embarrassing and time consuming ordeal that does not facilitate healthy reintegration into society. Thus, the discrete remote monitoring of a person under such a program by the court, or other authority, without requiring the monitored person to excuse themselves from society for more than a brief period of time would be useful in reintegrating the monitored person into society without the awkward and embarrassing effects of traditional monitoring procedures. Such a system is also useful to provide a system of monitoring where those monitored are emboldened to no longer feel like societal outcasts and are thus increasingly motivated to maintain their sobriety.

There are several methods for remotely determining the alcohol content (or level) of a person's breath using hand-held breathalyzer-type sobriety monitors. A common method is to use a breathalyzer device having a tin-oxide semiconductor alcohol sensor. The tin-oxide semiconductor alcohol sensor has the advantage of low cost at the expense of accuracy, alcohol specificity, and electrical power consumption. Another method is to employ the use of a breathalyzer device with an electrochemical fuel cell alcohol sensor. While this type of sensor tends to be more accurate, more alcohol specific, and utilizes less electrical power, the sensor itself has traditionally required the use of an active sampling mechanism such as a pump. The pump adds cost and size to the device, and utilizes electrical power. Specifically, current sample pump technology is largely based on solenoids, which utilize a significant amount of energy for actuation. Further, in battery-powered devices, the energy required to actuate the solenoid places a large drain on the battery and complicates the electronics.

An additional drawback of solenoid-based pumps is the inability to monitor the performance of the pump and determine whether it has failed through an end application. This is particularly important in devices which require high reliability, such as medical devices, or diagnostic/screening devices, such as a sobriety monitoring device.

Further, in application, breathalyzer solenoid-based pumps require a reservoir capacitor to rapidly deliver the energy required to actuate the solenoid typically add size to the device. This can be problematic for space-constrained designs, such as hand-held monitoring devices with physical size limitations, or designs in which it would be desirable to provide a less bulky or more discrete hand-held sobriety monitoring device.

It would therefore be desirable to provide methods, devices and systems of providing supervisory monitoring of sobriety that are discrete, portable, tamper-proof, and effective, and that can automatically alert a monitoring station of the need for attention and possible corrective or medical action by such a supervisory sober buddy or sober companion on an on-call basis. It would further be desirable to have such sobriety supervisory monitoring devices comprise a sample pump that removes the need for a reservoir capacitor and utilizes less volume, power consumption, and size. Additionally, it would further be desirable to monitor the performance of the sample pump so as to determine whether the monitoring device is functioning properly and providing accurate measurements.

SUMMARY OF THE INVENTION

Briefly, and in general terms, the present invention provides for systems, devices and methods for monitoring sobriety of a user on an automated basis, utilizing a hand-held breath testing device, a wireless or cellular transmitter or transceiver device for wirelessly transmitting results of the breath testing to a wireless or cellular receiver monitoring station. The monitoring station receives the breath testing results (and optionally identification such as a photograph) from the wireless or cellular transmitter or transceiver device, and indicates an alarm or otherwise alerts an on-call monitor when the wireless or cellular transmitter or transceiver is indicated to be off, or when the breath testing results indicate a breath test content greater than a predetermined threshold, or when the received breath is not the breath of the user (which can be determined from the photograph).

According to some aspects of the embodiments, the hand-held breath testing device can comprise a sample pump which utilizes a bellows assembly to draw in an air sample. Specifically, a trigger assembly having a bi-stable trigger spring, and a retraction assembly are used to expand the bellows and return the bellows to their original position. More specifically, the trigger assembly and retraction assembly comprise a trigger structure and a holding structure, respectively, which each comprise elements composed of a shape memory alloy, such as nitinol, that is flexible when cooled but returns to a pre-determined shape when heated. The bi-stable trigger spring and nitinol structure of the trigger assembly can be tightly integrated into or around the bellows so as to use less volume in the hand-held breath testing device or other air/gas sampling device. Further, the bi-stable trigger spring stores the energy required to actuate the bellows and, thus, further saves space within the device by removing the need for a reservoir capacitor. The nitinol-based sample pump and methods related thereto can be used in connection with other air sampling devices, medical devices, devices which require sampling of a measured volume of gas, or other devices of the like.

The embodiments described herein can be used in connection with a traditional sober buddy, chaperone service on an on-call basis only, to limit the expense and labor intensiveness of the supervisory care. Such a system may also be used to monitor abstinence from other drugs which can be taken orally and tested by breath analyzer or the like without the use of a chaperone on a continuing basis.

By using the methods, devices and system of the present invention, a family member trying to build back trust in family relationships can prove that they are making behavior changes by sending breath test reports on a predetermined schedule, or when randomly requested by the family. The present invention helps a person prove that they are making healthier choices in life and making steps toward rebuilding trust in family relationships. Families can benefit from knowing that loved ones are sober enough to drive, and the present invention can be used remotely to determine a person's sobriety or that blood alcohol levels are in an acceptable range. For families who want to monitor their children or spouses, the sobriety monitoring system of the present invention can send a breath test report directly to a mobile device such as a smartphone or tablet.

The present invention can also be used for immediate confirmation of an employee's alcohol level at any given time. Particularly those companies with employees who drive as a part of their employment would benefit by keeping their employees sober during working hours. The present invention also can be used in rehabilitative aftercare, and can be used to monitor multiple patients, and the present invention can be used by a sober companion during times when they are not able to accompany one or more of the patients.

Due to the compact, handheld portable nature of the present invention, the present invention mitigates the social stigma, personal embarrassment and general inconvenience typically associated with traditional sobriety monitoring techniques, e.g. ankle bracelets, urinalysis, fixed testing sites, etc.

Further, due to the nitinol-based sample pump, the present invention requires less volume and utilizes less power consumption. In addition, because the circuitry needed to heat the nitinol wire is less complex than the circuitry required for traditional sample pumps used with sobriety monitoring devices (e.g., solenoid based pumps), the present invention further provides a more cost-effective approach to sampling gasses in devices.

These and other aspects and advantages of the invention will be apparent from the following detailed description and the accompanying drawing, which illustrates by way of example the features of the invention.

BRIEF DESCRIPTION OF THE DRAWING(S)

Illustrated in the accompanying drawing(s) is at least one of the best mode embodiments of the present invention. In such drawing(s):

FIG. 5C is a left perspective view of the example embodiment of the sample pump illustrated in FIG. 5A, but with the bellows assembly removed for purposes of illustration, wherein FIG. 5C illustrates the bi-stable trigger spring in a post-triggered position.

DETAILED DESCRIPTION OF THE PREFERRED EMBODIMENTS

The above described drawing figures illustrate the invention in at least one preferred, best mode embodiment, which is further defined in detail in the following description. Those having ordinary skill in the art may be able to make alterations and modifications to what is described herein without departing from its spirit and scope. Therefore, it should be understood that what is illustrated is set forth only for the purposes of example and should not be taken as a limitation on the scope of the present system and method.

Described now in detail is a method, system, and device for monitoring sobriety of a user utilizing a sample pump according to at least one preferred embodiment.

Basic Structure

Figure 1A:
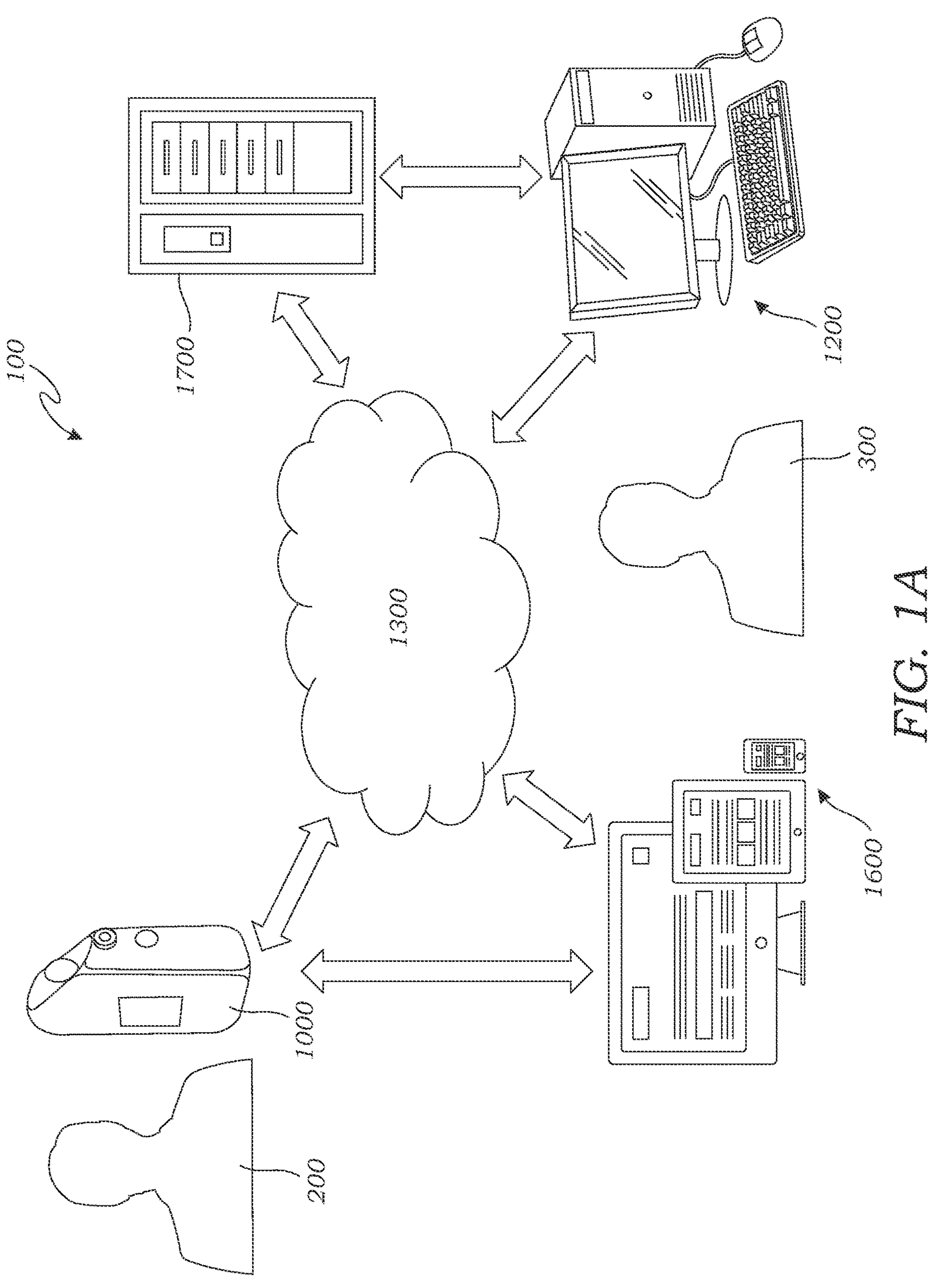
FIG. 1A is a schematic diagram of an example embodiment of a sobriety monitoring system in accordance with the present invention.

As shown in FIG. 1A, a schematic diagram of an example embodiment of a sobriety monitoring system 100 can include: a portable, handheld breath testing device 1000 communicatively coupled to a monitoring station 1200 and server 1700 via a wireless network 1300. The breath testing device 1000 tests the breath of a user 200 for the presence of alcohol and/or other substances. The breath testing device 1000 generates breath test data in response to assessment of the user's breath, the breath test data can indicate whether the user 200 has recently utilized alcohol and/or other substances. The breath test data can be wirelessly transmitted by the breath testing device 1000 via the network 1300 to the monitoring station 1200 and the server 1700, which may be any device or system at a location where the breath test data is received, including by way of non-limiting example: a cellular/smart phone, an email account, a website, a network database, and a memory device. The breath test data is stored by the monitoring station 1200, the server 1700 or both, and is retrievable therefrom by a monitor 300, such as a parent, guardian, parole officer, court liaison, spouse, sobriety coach, friend, sobriety monitoring company, or other authorized group, individual or combination thereof. In this manner, monitor 300 is able to respond appropriately to the detected utilization of alcohol and/or other substances by the user 200. Preferably, the monitor 300 is able to retrieve the breath test data via a network connected user interface device 1500, communicatively coupled-via the network 1300—to the monitoring station 1200, the server 1700 and/or to the breath testing device 1000.

Server 1700 can include applications distributed on one or more physical servers, each having one or more processors, memory banks, operating systems, input/output interfaces, and network interfaces, all known in the art. A plurality of user interface devices 1500 can be communicatively coupled to network 1300 such as a public network (e.g. the Internet and/or a cellular-based wireless network, or other network), a private network or a combination thereof. User interface devices 1500 and monitoring stations 1200 can include for example mobile devices (e.g. phones, tablets, or others) desktop or laptop devices, wearable devices (e.g. watches, bracelets, glasses, etc.), other devices with computing capability and network interfaces and so on. Sobriety monitoring system architecture 100 can include a network connected server system 1700 which can include hosting and/or interfacing, by way of physical servers, websites, webpages, web applications, social media platforms, advertising platforms, and others.

Figure 1B:
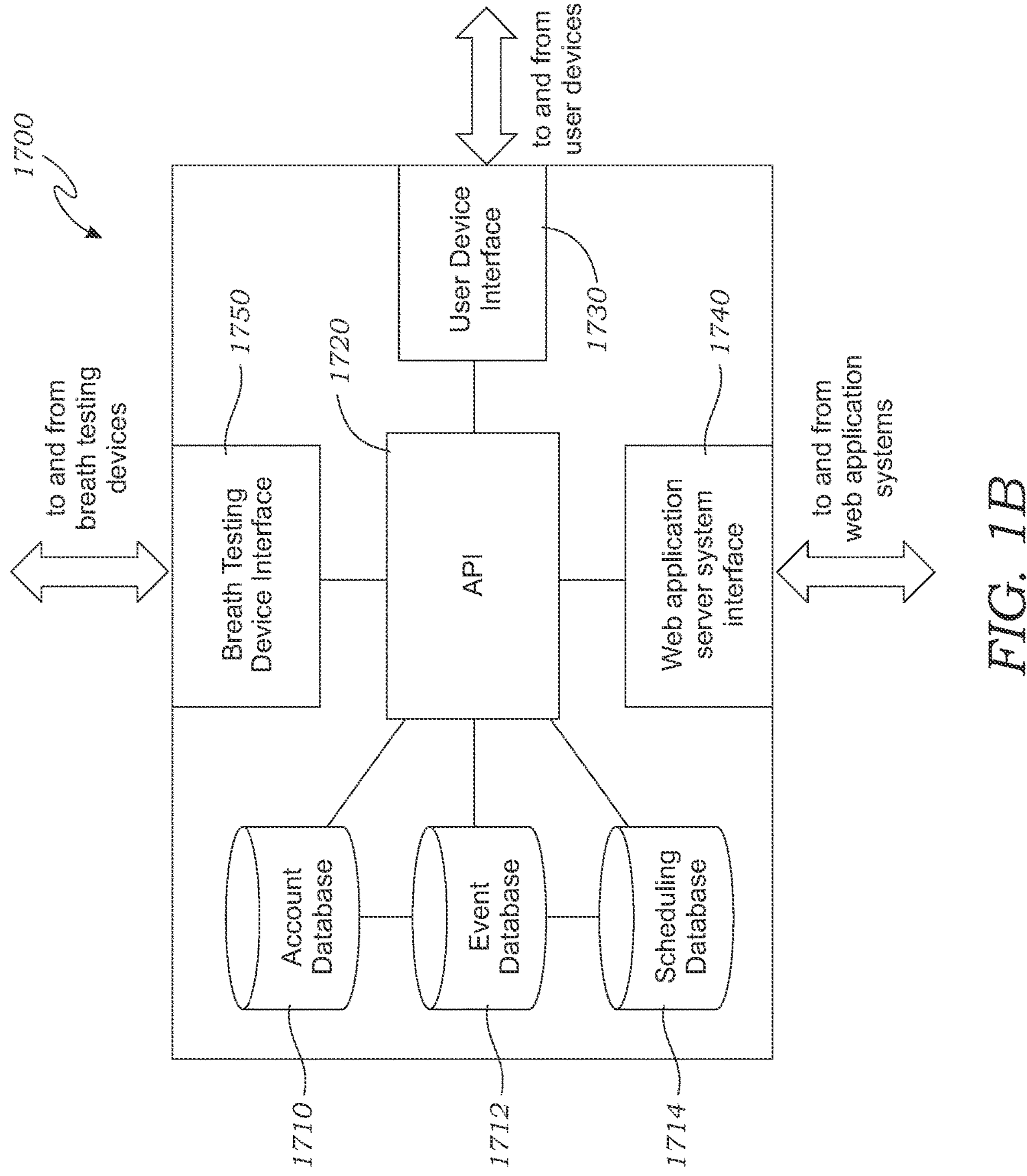
FIG. 1B is an example embodiment of a network connected server system in accordance with the present invention.

FIG. 1B shows an example embodiment of a diagram of a server system 1700 according to the invention including at least one user device interface 1730 implemented with technology known in the art for communication with user devices (e.g. user devices 1500 of FIG. 1A). The server system 1700 can also include at least one web application server system interface 1740 for communication with web applications, websites, webpages, websites, social media platforms, and others over a network. The server system 1700 can further include an application program interface (API) 1720 that is coupled to an account database 1710, event database 1712, and scheduling database 1714 and can communicate with interfaces such as the user device interface 1730, breath testing device interface 1750 and web application server system interface 1740, or others. The API 1720 can instruct the databases 1710, 1712, 1714 to store (and retrieve from the databases) information such as user account information, associated account information, event information or others as appropriate. The databases 1710, 1712, 1714 can be implemented with technology known in the art such as relational databases and/or object oriented databases or others.

Figure 1C:
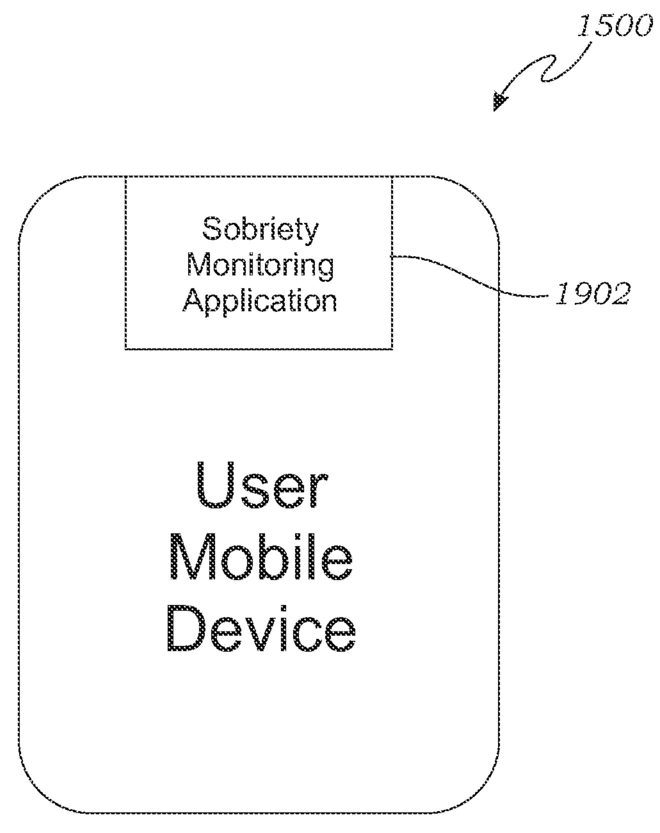
FIG. 1C is an example embodiment of a user device in accordance with the present invention.

FIG. 1C shows a diagram of a user device 1500 according to an embodiment of the invention that includes a network connected sobriety monitoring application 1902 that is installed in, pushed to, or downloaded to the user mobile device 1500. In many embodiments user mobile devices 1500 are touch screen devices such as smart phones or tablets. User mobile devices 1500 are implemented with memory, processors, communications links, power supplies such as rechargeable batteries, interfaces such as screens displaying graphical user interfaces ("GUIs"), buttons, touchpads, software stored in memory and executed by processors, audio input and output components, video input and output components, and others. Software can include computer readable instructions stored on non-transitory computer readable media such as computer memory.

In some embodiments, a server supported website comprises a mobile website accessible via a sobriety monitoring application 1902 on a personal computing device 1500 such as a mobile device (e.g. smart phone). The mobile website may be a modified version of the server supported website with limited or additional capabilities suited for mobile sobriety monitoring by monitor 300. In some embodiments no specific application 1902 is required but users can access a sobriety monitoring system through a web browser of the user mobile device 1500.

Figure 2:
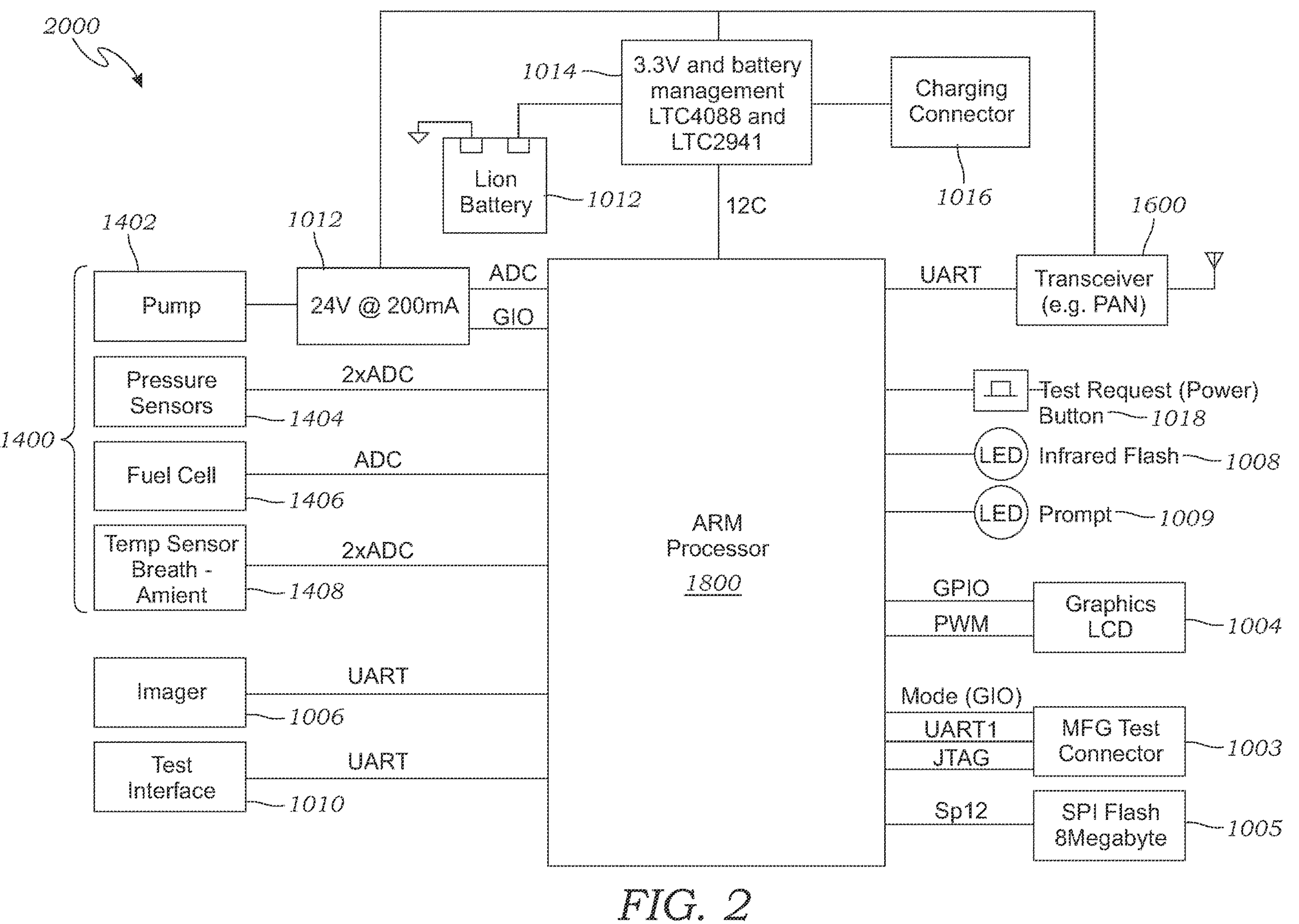
FIG. 2 is a schematic diagram of an example embodiment of a breath testing device in accordance with the present invention.

As shown in the example embodiment of FIG. 2, a breath testing device 1000 may comprise a memory 1005, such as a SPI FLASH 8 MB memory, communicatively coupled to a breath testing module 1400. Breath testing module 1400 is operable to measure the user's breath and convert the measurements into breath test data, as will be described elsewhere herein and breath testing module 1400 can be communicatively coupled to a wireless transceiver 1600, such as a personal area network (PAN). Each of memory 1005, breath testing module 1400 and transceiver 1600 can be communicatively coupled to a control unit 1800, such as an ARM processor, for controlling the operations thereof in accordance with the functionalities described herein. As breath testing device 1000 is portable and handheld, each of the components are preferably located within, immediately adjacent to, or exposed within and/or without, a device housing (e.g. housing 1002 of FIG. 3) whose dimensions are such that the breath testing device 1000—as a whole—may be discretely carried by the user, for example, within a pocket or small purse.

Further, as shown for example in the breath testing device architecture 2000 of FIG. 2, corresponding to a breath testing device 1000, may comprise: a central processing unit 1800 communicatively coupled to: a pump 1402, one or more pressure sensors 1404, a fuel cell 1406, and one or more temperature sensors 1408, which together can be included in a breath testing module 1400. An imager 1006, a test interface 1010, a flash memory 1005, a test connector 1003, a display 1004, an LED prompt 1009, a flash LED 1008, a test request/power button 1018, a wireless transceiver 1600, batteries 1012 and 1014, and associated charging interface 1016 can also be communicatively coupled to central processing unit 1800. Pump 1402 can also be connected through a converter 1012 to transceiver 1600. Each of these components are described further herein in the context of their functionalities within the described embodiments.

In an example embodiment, a monitoring station 1200, as shown for example in FIG. 1A, can comprise a server system 1700, hosting a server supported website (not shown). Server supported website can be supported by a server system 1700 comprising one or more physical servers, each having a processor, a memory, an operating system, input/output interfaces, and network interfaces, all known in the art, coupled to the network 1300. The server supported website can comprise one or more interactive web portals through which a monitor 300 may monitor the sobriety of a user 200 using a breath monitoring device 1000, in accordance with the described embodiments. In particular, the interactive web portals may enable the monitor 300 to retrieve breath test reports generated using data from the breath testing devices 1000 of one or more users (e.g. user 200), set or modify breath test schedules, and/or set or modify preferences. Preferably, the interactive web portals are accessible via a personal computing device 1500, such as for example, a home computer, laptop, tablet, and/or smart phone.

Additional details of these features and others may be found in U.S. Pat. No. 8,707,758, issued on Apr. 29, 2014; U.S. Pat. No. 8,381,573, issued on Sep. 15, 2010; and U.S. application Ser. No. 13/274,553, filed on Oct. 17, 2011, the entire disclosures and contents of which are herein incorporated by reference in their entirety.

Breath Characteristic Data

In some embodiments, the breath testing device 1000 comprises one or more sensors for determining characteristics of the user's breath such as pressure (see e.g. FIG. 2 pressure sensor(s) 1404) and/or temperature (see e.g. FIG. 2 Temp sensor Breath+Ambient 1408), which may be utilized to generate breath characteristic data. The breath characteristic data may in turn be utilized to determine whether the breath testing device 1000 has been tampered or otherwise interfered with in a way that would compromise the breath testing data.

Figure 4:
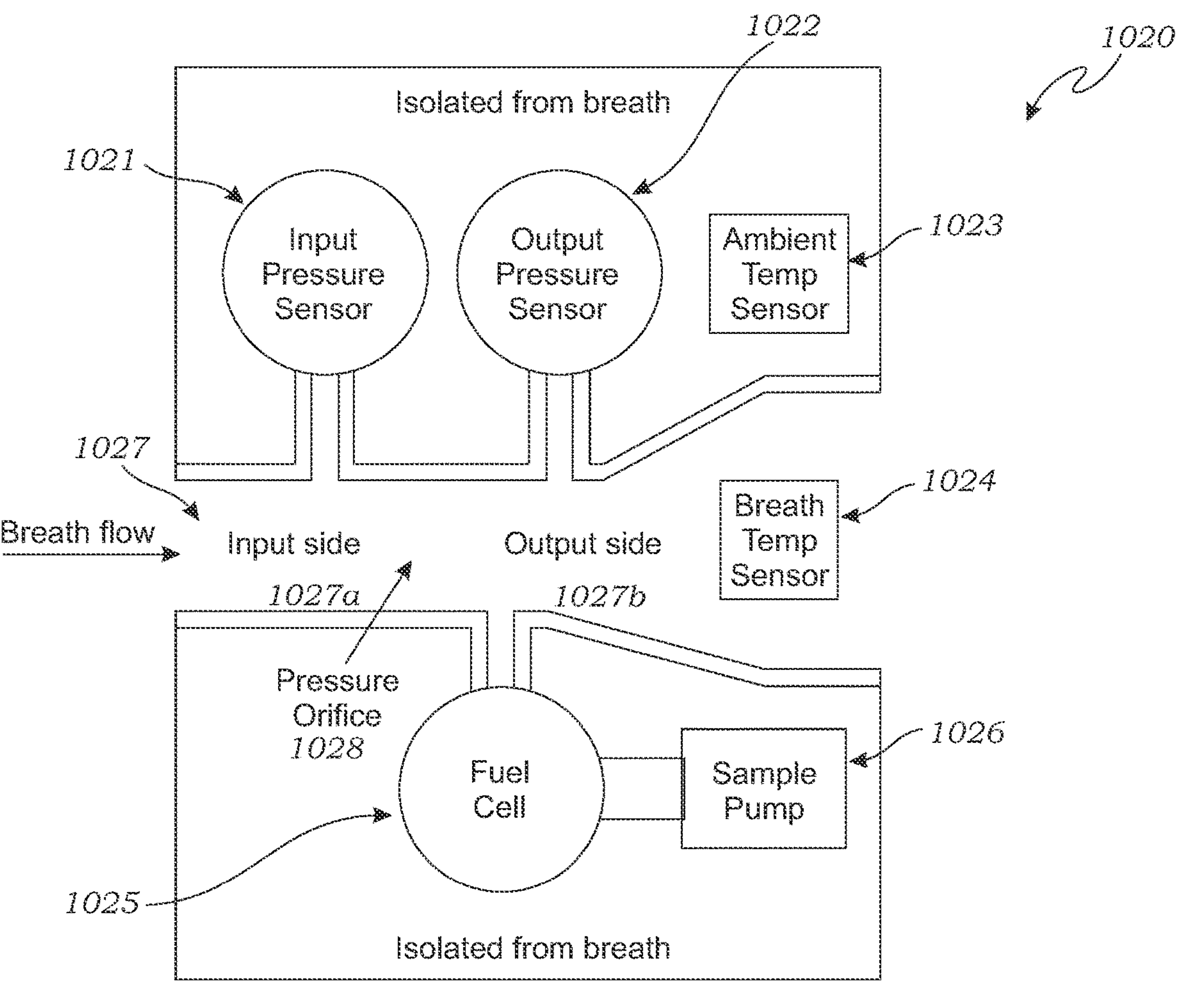
FIG. 4 is a schematic of an example embodiment of a breath intake of a breath monitoring device in accordance with the present invention.

FIG. 4 illustrates a schematic diagram of an exemplary breath intake 1020 comprising: an input pressure sensor 1021, an output pressure sensor 1022, an ambient temperature sensor 1023, a breath temperature sensor 1024, a fuel cell 1025, a sample pump 1026 and a breath chamber 1027, including an input chamber 1027(*a*) partially separated from an output chamber 1027(*b*) by a pressure orifice 1028. As shown in FIG. 4, various components can be isolated or coupled with each other and/or breath areas as necessary. In an example embodiment, a user 200 breathes into input chamber 1027(*a*) and the breath leaves the device 1000 via output chamber 1027(*b*).

In some embodiments, the breath temperature sensor 1024 can detect the temperature of an airflow during an administered breath test, while an ambient temperature sensor 1023 can detect an ambient temperature of non-tested air, isolated from the breath flow. The pressure sensors 1021 and 1022 can detect the pressure of an airflow between the input side 1027(*a*) and the output side 1027(*b*) of chamber 1027 of breath applied during an administered breath test. Each of these components may be individually or collectively used to detect airflow tampering by a user 200.

As an example, human breath is generally no colder than thirty-three degrees Celsius, while compressed air from a container or other source may be significantly colder. Should a user 200 attempt to tamper with a scheduled breath test by 'blowing' into the breath testing device 1000 with compressed air, the breath temperature sensor may generate breath characteristic data indicating that the breath testing device has been tampered with accordingly. Moreover, the ambient temperature may be measured by ambient temperature sensor 1023 and used to further verify 'human breath' is being applied by comparing a measured temperature value with a temperature value measured by the breath temperature sensor 1024 using a processor and comparing with a threshold, range or other set of values to verify accuracy. For example, human respiration typically heats human breath temperature to at least fifteen degrees Celsius. If a measured ambient temperature is between ten and fifteen degrees Celsius, human respiration typically heats the breath temperature to at least twenty degrees Celsius. If the ambient temperature is above fifteen degrees Celsius, human respiration typically heats the breath temperature to at least twenty-eight degrees Celsius. When the ambient temperature is above thirty-three degrees Celsius, human respiration measured by the breath temperature sensor will typically be cooler than the ambient temperature. The temperature sensors 1023, 1024 may also be coupled with or include timers (not shown) detect time variances in temperature. Such time variances may indicate, for example, the presence of a heated air source that is heating up.

As an additional example, should a user block airflow from the output side 1027(*b*) of chamber 1027 to an exterior of the device 1000, the pressure in the output side 1027(*b*) of chamber 1027 would tend to increase relative to the pressure in the input side 1027(*a*) of the chamber 1027. The pressure sensors 1021, 1022 may detect this tampering and, when compared using a processor and programmed thresholds, ranges or other sets of values, generate breath characteristic data that indicates this tampering accordingly.

Sample Pump

Figures 5A, 5B:
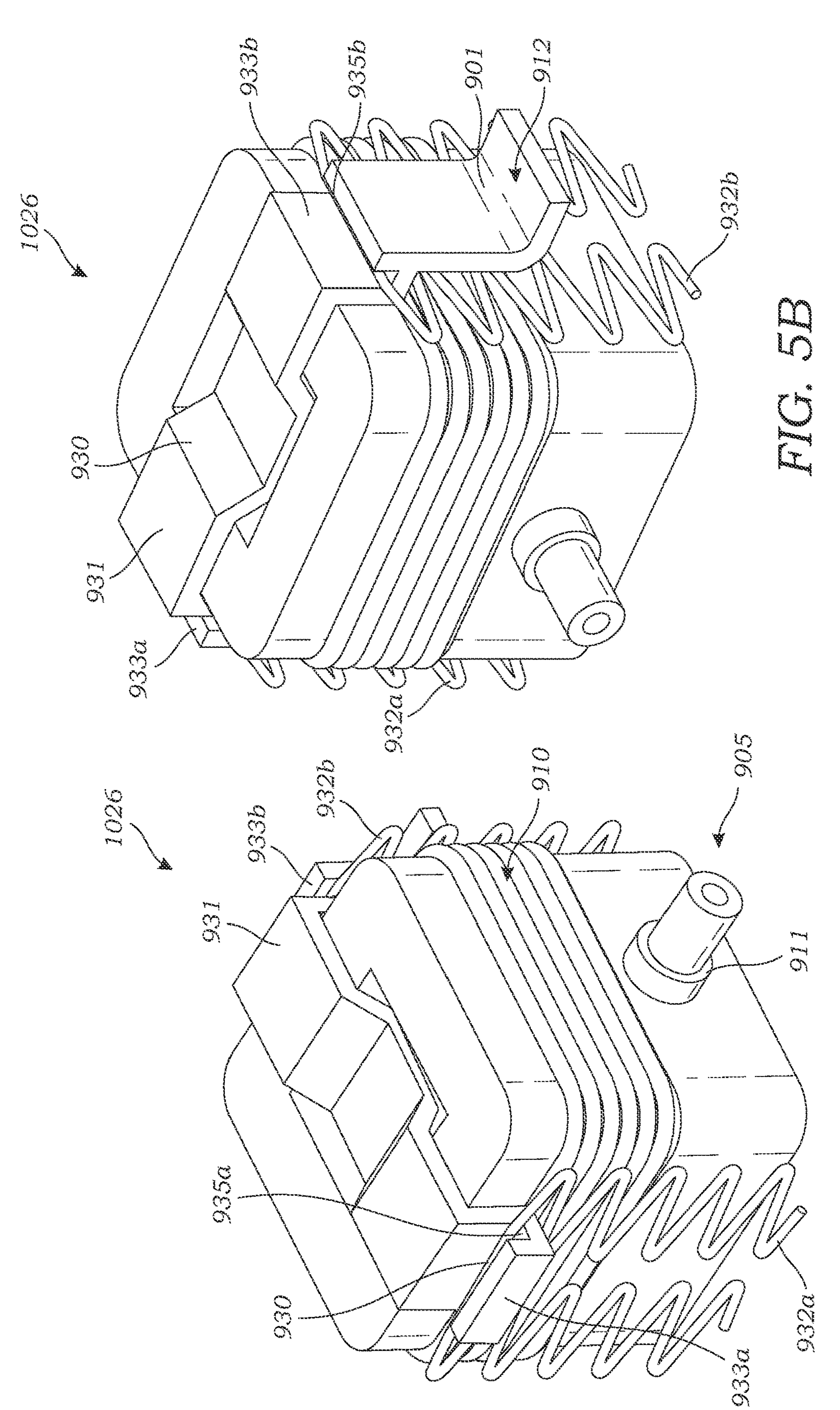
FIG. 5A is a left perspective view of an example embodiment of a sample pump in accordance with the present invention.
FIG. 5B is a right perspective view of the example embodiment of the sample pump illustrated in FIG. 5A.
Figure 5C:
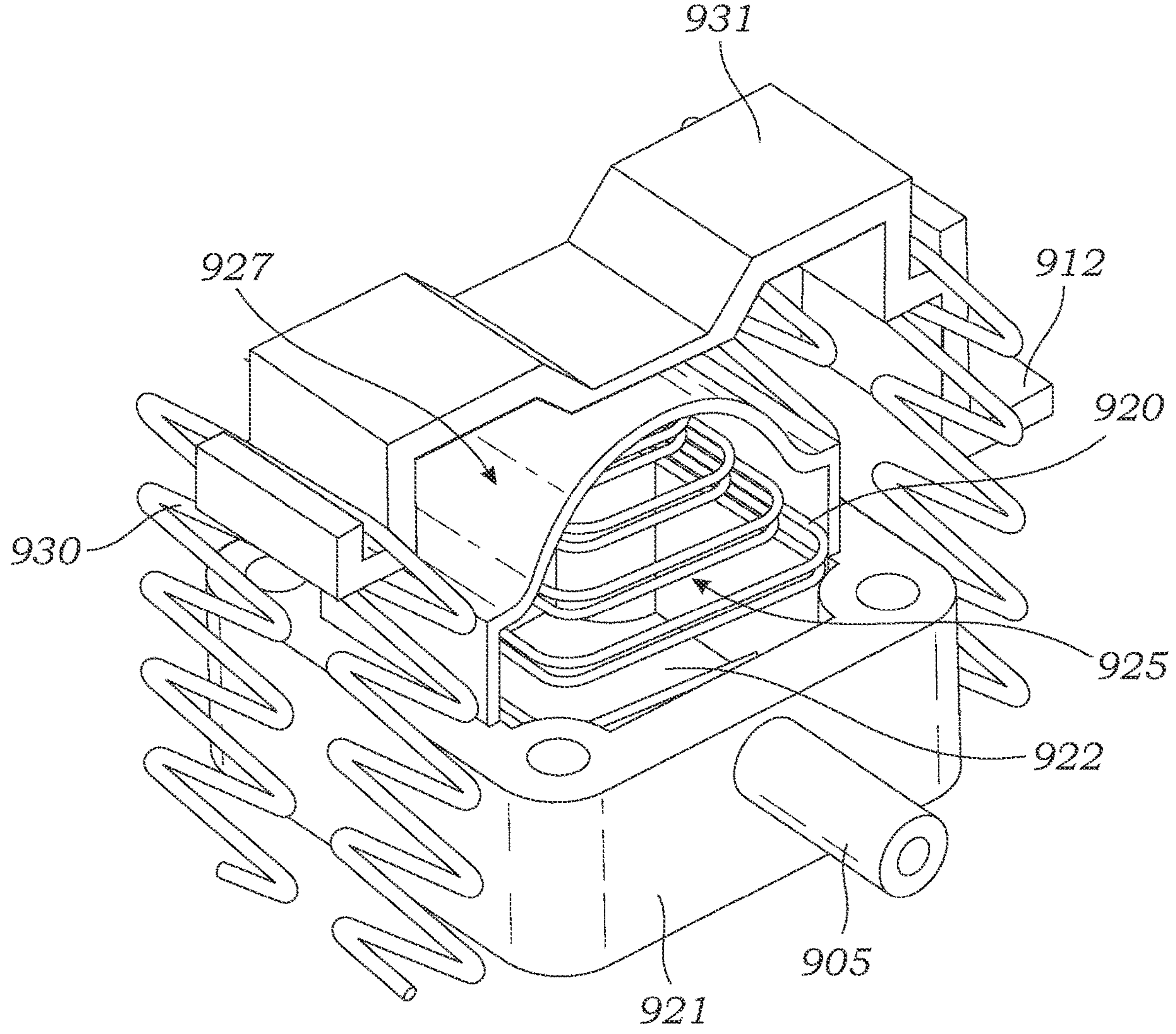

With reference to FIGS. 5A-5C, example embodiments of sample pump 1026 will now be described. FIGS. 5A-5C illustrate a sample pump 1026 which can be utilized with any of the embodiments described herein or incorporated by reference. Further, those of skill in the art will recognize that the sample pump 1026 embodiments described herein can be utilized with other diagnostic or screening devices, medical devices, or air/gas sampling devices.

In some embodiments, the breath testing device 1000 comprises the sample pump 1026. Sample pump 1026 can be configured within the device housing 1002 of breath testing device 1000, depicted in FIG. 3. According to an aspect of the embodiment, and with reference to FIGS. 5A-5C, the sample pump 1026 can comprise an inlet port 905, a flexible bellows assembly 910, a trigger assembly 920, and a retraction assembly 930.

Specifically, the sample pump 1026 uses the bellows assembly 910 to draw an air sample into sample pump 1026 through the inlet port 905. The bellows 910 arrangement is positioned outside of a rigid frame 921 (shown in FIG. 5C) that surrounds the inner perimeter of the bellows 910. In some embodiments, and as best depicted in FIGS. 5C, the rigid frame 921 can have four walls which form an interior chamber 922. According to an aspect of the embodiments, the rigid frame 921 is configured to provide structural support for the bellows 910 as they expand and compress in response to actuation of the pump 1026. In some exemplar embodiments, the shape of the pump 1026 and rigid frame 921 can be complementary to one another. In some embodiments, the rigid frame 921 can form a quadrilateral shape. Moreover, and as illustrated in FIGS. 5A-5B, the pump 1026 can form a quadrilateral shape and/or be prismatic. In exemplar embodiments, the pump 1026 can form a cuboid or rectangular shape. Those of skill in the art will recognize that other shapes, dimensions and configurations of the rigid frame 921 and/or pump 1026 can be determined without departing from the scope of the present disclosure.

As best illustrated in FIGS. 5A-5C, in some embodiments, the inlet port 905 extends from one of the four walls of the rigid frame 921. Specifically, the inlet port 905 extends outwardly from an exterior surface of one of the four walls. More specifically, the pump 1026 includes an opening 911 sized and configured for receipt of the inlet port 905 such that the inlet port 905 can protrude from the rigid frame

921 and extend outwardly from the pump 1026 so as to be at least partially external relative to the bellows 910.

According to an aspect of the embodiments, and with reference to FIG. 5C, the trigger assembly 920 is housed within an interior of the bellows assembly 910 and comprises a trigger structure 925 and a bi-stable trigger spring 927. Preferably, the trigger structure 925 is formed from a shape memory alloy material having a wire structure. More preferably, the shape memory alloy is nickel-titanium alloy popularly known as "nitinol." Nitinol wire is preferred due to its unique properties of undergoing deformation at a particular temperature, and then recovering to its original, undeformed shape when heated above a transformation temperature (in some embodiments, the transformation temperature for nitinol can be between, e.g., 30° C. to 130° C.). For example, in some embodiments, the nitinol wire of the trigger structure 925 is flexible when cool, but returns to its predetermined shape when heated above its transformation temperature.

According to another aspect of the embodiments, passage of a small electric current through the nitinol wire of the trigger structure 925 is sufficient to heat the shape memory alloy so as to heat the nitinol wire above its transformation temperature. In this regard, the trigger structure 925 can transform in shape in response to current passing therethrough. Those of skill in the art will recognize that other shape memory alloys or materials or the like can be used. Those of skill in the art will further recognize that other structures for the trigger structure 925 can be utilized without departing from the scope of the disclosure.

In some embodiments, and as best shown in FIG. 5C, the interior chamber 922 of the rigid frame 921 is further configured to house at least a portion of the trigger assembly 920. In this regard, the trigger assembly 920 is internal relative to the bellows 910. Further, in this manner, the sample pump 1026 and components thereof utilize less volume within the device than traditional sample pumps.

Specifically, and still with particular reference to FIG. 5C, the bi-stable trigger spring 927 is configured to extend upwardly from an upper surface of the rigid frame 921. More specifically, in some embodiments, the trigger structure 925 is arranged such that at least a portion thereof is received within the interior chamber 922 of the rigid frame 921, and can extend outwardly in a proximal direction relative to the rigid frame 921. Even more specifically, the bi-stable trigger spring 927 can be immediately adjacent to and operatively coupled with the trigger structure 925. In some embodiments, at least a portion of the bi-stable trigger spring 927 is configured to at least partially overlay the trigger structure 925. As such, as the trigger structure 925 extends outwardly in a proximal direction relative to the rigid frame 921, it can interface with the bi-stable trigger spring 927, thereby exerting a force thereon so as to cause the bi-stable trigger spring 927 to change position.

According to an aspect of the embodiments, the bi-stable trigger spring 927 can transition between a pre-triggered position and post-triggered position. In some embodiments, the bi-stable trigger spring 927 is configured such that, in its pre-triggered position, it comprises an arch having convex portion with an apex pointing downwardly towards the trigger structure 925 (the pre-triggered position of the bi-stable trigger spring is not shown). In its pre-triggered position, the shape of the bi-stable trigger spring 927 is such that it can change in response to a force exerted by the trigger structure 925. In some embodiments, and as shown FIG. 5C, the bi-stable trigger spring 927 is further configured such that, in its post-triggered position, the arch inverts so as to have a concave portion with an apex pointing upwardly towards an upper, interior wall of the bellows 910 (bellows 910 not depicted in FIG. 5C). In this regard, the shape of the bi-stable trigger spring 927 in its post-triggered position is such that it can exert an upward force onto the bellows 910 so as to cause the bellows 910 to expand or stretch.

According to another aspect of the embodiments, the bi-stable trigger spring 927 is configured such that it transitions between the pre-triggered position and the post-triggered position as a function of the trigger structure 925 undergoing shape transformation. In some embodiments, the bi-stable trigger spring 927 is configured to be in its pre-triggered position until pushed beyond a trigger point by the trigger structure 925. Even more specifically, the bi-stable trigger spring 927 is configured such that it is in the pre-triggered position prior to the current being applied to the trigger structure 925 (when the nitinol wire is below transformation temperature). Moreover, the bi-stable trigger spring 927 is configured such that it is in its post-triggered position after the current is applied to the trigger structure 925 and the nitinol wire of the trigger structure 925 has exceeded its transformation temperature. In some embodiments, the trigger point is reached upon the trigger structure 925 reaching the transformation temperature of the nitinol wire. In some embodiments, the current is applied to the trigger structure 925 via a battery. Those of skill in the art will recognize that other means or circuitry can be provided for applying current to the trigger structure 925.

In this regard, as sufficient current is applied to the trigger structure 925 so as to cause it to transform into a predetermined shape, the trigger structure 925 is configured such that the predetermined shape is such that it is capable of exerting an upward force on the bi-stable trigger spring 927, thereby causing the bi-stable trigger spring 927 to transition from its pre-triggered position to its post-triggered position. As such, upon the bi-stable trigger spring 927 being pushed beyond its trigger point, and as the bi-stable trigger spring 927 transitions from its pre-triggered position to its post-triggered position, it begins to extend upwardly and push on the interior wall of bellows 910, thereby causing the bellows 910 to expand or stretch. In this regard, as the bellows 910 expand, the pump 1026 is actuated and air is drawn into the pump 1026. Further, because the energy needed to actuate the bellows 910 is stored in the bi-stable trigger 927, the sample pump 1026 does not require a reservoir capacitor.

According to an aspect of the embodiments, the rigid frame 921 maintains and stabilizes the position of the bellows 910, so that as the bi-stable trigger spring 927 transitions between its pre-triggered position and post-triggered position, the bi-stable trigger spring 927 can move along a straight line. In some embodiments, this prevents the bi-stable trigger spring 927 from deforming or cocking during transition to prevent volumetric variations in the volume of the air sample in the pump 1026.

According to another aspect of the embodiments, as the bellows 910 expand, the internal pressure and distance by which the bellows 910 have stretched from its original position can be monitored by the sobriety monitoring application 1902 or through the web browser of the user mobile device 1500. Specifically, in some embodiments, an internal pressure sensor is arranged within the pump 1026 so as to measure the pressure change as the bellows 910 expand and compress. In some embodiments, the internal pressure sensor can be a digital sensor which is communicatively coupled to the sobriety monitoring application 1902 and/or user mobile device 1500. In some embodiments, the internal pressure sensor can additionally operate in like manner to the output pressure sensor 1022, and detect the airflow pressure on the output side 1027(*b*) of chamber 1027 of breath applied during an administered breath test. Further, in some embodiments, the pump 1026 further comprises a reflective surface 912 anchored to an exterior surface of the pump 1026, on a top portion of the bellows 910, so as to allow a sensor to measure the distance travelled when the bellows 910 expand. In some embodiments, and as best illustrated in FIG. 5B, the reflective surface 912 is integrated with or extends from a holding structure 931 of the retraction assembly. The reflective surface 912 includes a flange portion 901 configured to extend outwardly in a horizontal direction away from the pump 1026.

According to an aspect of the embodiments, the breath testing device 1000 can comprise a light emitting diode (LED) and receiver configured to emit infrared light. Specifically, the infrared light can emit onto the flanged portion 901 of the reflective surface 912. Further, the breath testing device 1000 can further comprise a sensor adjacent to the emitter configured to detect the reflection off the reflective surface 912. Depending on the strength of the reflection detected by the sensor, the sensor can determine the distance of the reflective surface 912 from the LED. In this regard, the sensor and reflective surface 912 help determine whether the pump 1026 has been actuated and the bellows 910 have been fully expanded.

In some embodiments, when the bellows 910 are fully stretched or expanded, the pump 1026 can be about 0.7 inches in height, 0.7 inches in width, and 0.7 inches in length. In some embodiments, when the bellows 910 are fully expanded, the pump 1026 has a volume of about 0.343 inches$^3$. Those of skill in the art will recognize that pumps 1026 having other dimensions and volumes can be utilized without departing from the scope of the disclosure.

Further, once the pump 1026 has been actuated and the bellows 910 have been fully stretched, the retraction assembly 930 is configured to return the pump 1026 to its original or pre-triggered state (e.g., FIGS. 5A-5B). According to an aspect of the embodiments, and as depicted in FIGS. 5A-5B, the retraction assembly 930 is configured along the exterior surface of the pump 1026 so as to be external relative to the bellows 910. Preferably, the retraction assembly 930 comprises a holding structure 931 that supports one or more wire elements 932*a*, 932*b* formed from a shape memory alloy material. More preferably, the holding structure 931 supports one or more wire elements 932*a*, 932*b* composed of nitinol. In this regard, and in like manner to the nitinol wire of the trigger assembly 920, the nitinol wires of the retraction assembly 930 undergo deformation at a particular temperature, and then recover to their original, undeformed shape when heated above a transformation temperature. Those of skill in the art will recognize that the transformation temperature(s) for the nitinol wire of the trigger assembly 920 may vary from the transformation temperature(s) for the nitinol wire(s) of the retraction assembly 930.

In some embodiments, and with reference to FIGS. 5A-5B, the holding structure 931 comprises at least two nitinol wire elements 932*a*, 932*b*. More specifically, in some embodiments, a first wire element 932*a* is configured along a first side of the pump 1026 and a second wire element 932*b* is configured along a second side of the pump 1026. More specifically, the first side is opposite to the second side.

Specifically, in some embodiments, the holding structure 931 further comprises one or more hooking features 933*a*, 933*b* extending from opposite ends thereof (see. e.g., FIGS. 5A-5B). In some embodiments, the holding structure 931 comprises two hooking features 933*a*, 933*b*. Specifically, the holding structure 931 is anchored on a top surface of the pump 1026, and the first hooking feature 933*a* is configured such that it extends from the top surface downwardly along the first side of the pump 1026, and a second hooking feature 933*b* is configured such that it extends from the top surface downwardly along the second side of the pump 1026. The first hooking feature 933*a* comprises a first groove 935*a* configured to hold or support a portion of the first wire element 932*a*. In like manner, the second hooking feature 933*b* comprises a second groove 935*b* configured to hold or support a portion of the second wire element 932*b*. In this regard, the hooking features 933*a*, 933*b* maintain displacement of the nitinol wire elements 932*a*, 932*b* in a lateral direction as the nitinol wire elements 932*a*, 932*b* transform in response to the passage of current and temperature cycling. In exemplar embodiments, current passes through both the nitinol wire elements 932*a*, 932*b* contemporaneously and with the same energy.

Specifically, the bellows 910 return to their original, compressed state as sufficient current passes through the nitinol wire elements 932*a*, 932*b* of the holding structure 931 so as to cause the nitinol wire elements 932*a*, 932*b* to reach and exceed their transformation temperature. More specifically, as the nitinol wire elements 932*a*, 932*b* reach and exceed their transformation temperature, the nitinol wire elements 932*a*, 932*b* are configured to compress, thereby exerting a downward force on the grooves 935*a*, 935*b*, causing the holding structure 931 on the top surface of the pump 1026 to push down on and compress the bellows 910.

In some embodiments, the current is applied to the nitinol wire elements 932*a*, 932*b* via a battery. In some embodiments, the same battery can be utilized to provide current to both the trigger structure 925 and to the nitinol wire elements 932*a*, 932*b*. In other embodiments, a first battery can be utilized to provide current to the trigger structure 925 and a second battery can be utilized to provide current to the nitinol wire elements 932*a*, 932*b*. Those of skill in the art will recognize that other means or circuitry can be provided for applying current to the nitinol wire elements 932*a*, 932*b*.

According to an aspect of the embodiments, current is not applied to the nitinol wire elements 932*a*, 932*b* at the same time as current is applied to the trigger structure 925. In this regard, the bellows 910 can expand without being met with additional resistance from the nitinol wire elements 932*a*, 932*b* reacting to current. In like manner, current is not applied to the trigger structure 925 when current is applied to the nitinol wire elements 932*a*, 932*b*. As such, the bellows 910 can compress without being met with additional resistance from the trigger structure 925. In this manner, the bi-stable trigger spring 927 can return to its pre-triggered position as the bellows 910 compress.

Because current is not applied to the nitinol wire elements 932*a*, 932*b* at the same time as current is applied to the trigger structure 925, the trigger structure 925 can heat as the nitinol wire elements 932*a*, 932*b* remain cool or release heat/become cooler. Similarly, because current is not applied to the trigger structure 925 at the same time as current is applied to the nitinol wire elements 932*a*, 932*b*, the nitinol wire elements 932*a*, 932*b* can heat as the trigger structure 925 remains cool or releases heat/becomes cooler in temperature. In this regard, the pump 1026 is able to expand and compress as a function of current being applied to the nitinol elements of the trigger assembly 920 and retraction assembly 930, respectively.

Testing

As discussed herein with reference to FIG. 1, the breath testing device 1000 tests the breath of the user 200 for the presence of alcohol and/or other substances, generating breath test data in response to receiving the user's breath and analyzing it. The breath test data is then transmitted to the monitoring station 1200, server 1700, user device 1500, or a combination thereof, preferably via wireless transmission over the network 1300.

During a breath test, the breath testing device 1000 receives a user's breath, analyzes the user's breath and converts this information into breath test data to be transmitted to the monitoring station 1200, server 1700, user device 1500, or a combination thereof. The breath test data preferably reflects the blood alcohol content ("BAC") of the user 200 during the breath test, or an indication of whether the user's BAC is above or below a certain BAC threshold. The BAC threshold may be set and modified by the monitor 300 via the server supported website.

Figure 3:
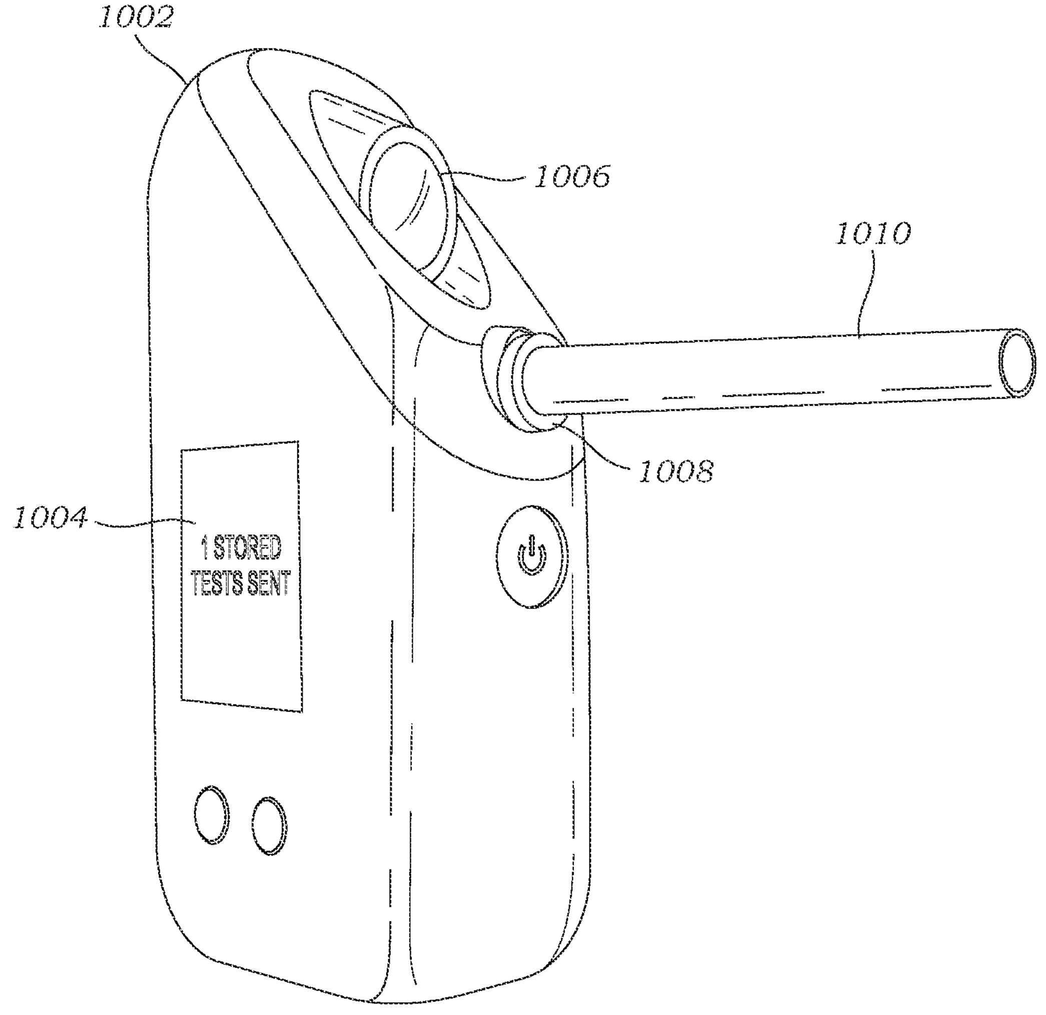
FIG. 3 is a perspective view of an example embodiment of a breath testing device in accordance with the present invention.

Additionally, the breath test data may be displayed on the breath testing device 1000 via the display screen 1004 located exterior to the device housing 1002, as shown in FIG. 3, for example. Alternatively, or in addition, a visual prompt may be generated based on the breath test data and displayed on the display screen 1004 of the breath testing device 1000, the visual prompt indicating a 'pass,' 'fail,' 'missed,' or 'inconclusive' result of the breath test. Moreover, in the event of either a 'fail' or 'inconclusive' breath test, the visual prompt may also instruct the user 200 to re-administer a breath test.

Additional details of these features and others may be found in U.S. Pat. No. 8,707,758, issued on Apr. 29, 2014; U.S. Pat. No. 8,381,573, issued on Sep. 15, 2010; and U.S. application Ser. No. 13/274,553, filed on Oct. 17, 2011, the entire disclosures and contents of which are herein incorporated by reference in their entirety.

User Verification Features

User identification data for a particular user 200 can include or consist of data utilized by the system to verify the identity of the user 200 taking a breath test using a particular breath monitoring device 1000. The user identification data may comprise one or more of: image data, video data, biometric data (e.g. fingerprint, DNA, retinal scan, etc. data), username/password entry data, or any other type of data that may be used to verify the identity of the user taking the breath test. This verification is useful to make it more difficult for non-users to administer the scheduled breath test (to themselves) in lieu of the particular monitored user 200, i.e. to curtail cheating. Where the user identification data indicates that a non-user has administered the scheduled breath test in lieu of the user 200, the breath test report generated therefrom may identify the administered breath test as a 'fail' event. In some embodiments, this can trigger unique "attempted cheating" alerts.

As reflected for example in FIG. 3, in some embodiments, a breath testing device 1000 comprises a test interface 1010 (see e.g. breath intake 1020 of FIG. 4), for receiving the user's breath during the scheduled breath test, and a camera or imager 1006 substantially adjacent the breath intake or otherwise positioned so as to capture an image of the user 200 during a breath test. Preferably, the camera 1006 is equipped with a lens capable of capturing the entire face of the user at close distances, such as a fish-eye lens. The captured image may be converted into image data to be transmitted to the monitoring station 1200, stored by server 1700 and/or utilized to verify the identity of the user taking the breath test.

Additional details of these features and others may be found in U.S. Pat. No. 8,707,758, issued on Apr. 29, 2014; U.S. Pat. No. 8,381,573, issued on Sep. 15, 2010; and U.S. application Ser. No. 13/274,553, filed on Oct. 17, 2011, the entire disclosures and contents of which are herein incorporated by reference in their entirety.

Device Location Features

Device location data in some embodiments includes or consists of data utilized by the system to establish the geographical location of a breath testing device 1000. The device location data may comprise one or more of: global positioning system ("GPS") data, Assisted GPS ("A-GPS") data, and Advanced Forward Link Trilateration ("AFLT") data. Many appropriate hardware/software components for generating the aforementioned device location data are known in the art. The device location data may be useful to verify the location of the user 200 during an administered breath test. Additionally, the device location data may be useful to verify the location of the breath testing device 1000 in the event it becomes lost or otherwise misplaced. Accordingly, the device location data may be transmitted to the monitoring station 1200, server 1700, and/or user devices 1500 independent of some or all breath test data, for example, during a periodic check-in with the monitoring station 1200, server 1700, and/or user devices 1500.

In some embodiments, location data is utilized by monitoring station 1200, server 1700, and/or user devices 1500 to record the geographic location of the breath testing device 1000 and in can be stored on monitoring station 1200, server 1700, and/or user devices 1500. The monitor 300 (and/or user 200) may access the location data via the interactive web portal, so as to track the location of the breath testing device 1000 at least when the device 1000 is administering a test. In this manner, the monitor 300 (and/or user 200) may determine the location of the breath testing device 1000. This feature may be useful to, for example, locate misplaced breath testing devices 1000, or track the location of the user 200, for example, if the user 200 is on house-arrest or some other form of detention.

Additional details of these features and others may be found in U.S. Pat. No. 8,707,758, issued on Apr. 29, 2014; U.S. Pat. No. 8,381,573, issued on Sep. 15, 2010; and U.S. application Ser. No. 13/274,553, filed on Oct. 17, 2011, the entire disclosures and contents of which are herein incorporated by reference in their entirety.

Device Status Features

Device status data can include or consist of data reflecting the operation status and parameters of the breath testing device 1000. As discussed herein, the breath testing device 1000 may periodically connect to a monitoring station 1200, server 1700, and/or user devices 1500 via the network 1300 so as to transmit—or otherwise exchange-data therewith. During this data transmission, the breath testing device 1000 may then transmit device status data to the monitoring station 1200, server 1700, and/or user devices 1500, which may include, for example, calibration data and/or security data.

In some embodiments, the periodic 'check-in' may occur according to predetermined time intervals. For example, the 'check-in' may coincide with the scheduled breath test. Alternatively, or in addition thereto, the 'check-in' may occur according to a schedule as, for example, every few hours, or minutes. In some embodiments, the periodic 'check-in' may occur every 5 minutes. However, if the 'check-in' fails, for example, due to failed network connectivity, the subsequent 'check-in' may be rescheduled according to one or more backup time intervals. For example, if the 5 minute check-in fails, the 'check-in' period may be reset to occur every 15 minutes, 30 minutes, or 60 minutes. In this way, the breath testing device 1000 may conserve battery life during extended periods of connectivity. In some embodiments, when connectivity is reestablished, the 'check-in' period may be automatically reset to the default period.

As discussed herein, during the 'check-in,' any data stored in device 1000 memory to be transmitted may be transmitted to a monitoring station 1200.

Additional details of these features and others may be found in U.S. Pat. No. 8,707,758, issued on Apr. 29, 2014; U.S. Pat. No. 8,381,573, issued on Sep. 15, 2010; and U.S. application Ser. No. 13/274,553, filed on Oct. 17, 2011, the entire disclosures and contents of which are herein incorporated by reference in their entirety.

Bluetooth

In some embodiments, a breath testing device 1000 may transmit the breath test data to an intermediary device, such as cellular phone, which in turn transmits the breath test data to a monitoring station 1200 via a network 1300 as shown for example in FIG. 1. Accordingly, a local network may comprise a PAN, and the transceiver may comprise a personal-area-network transceiver (e.g. transceiver 1600 of FIG. 2). This can be part of or separate from network 1300.

Figure 6:
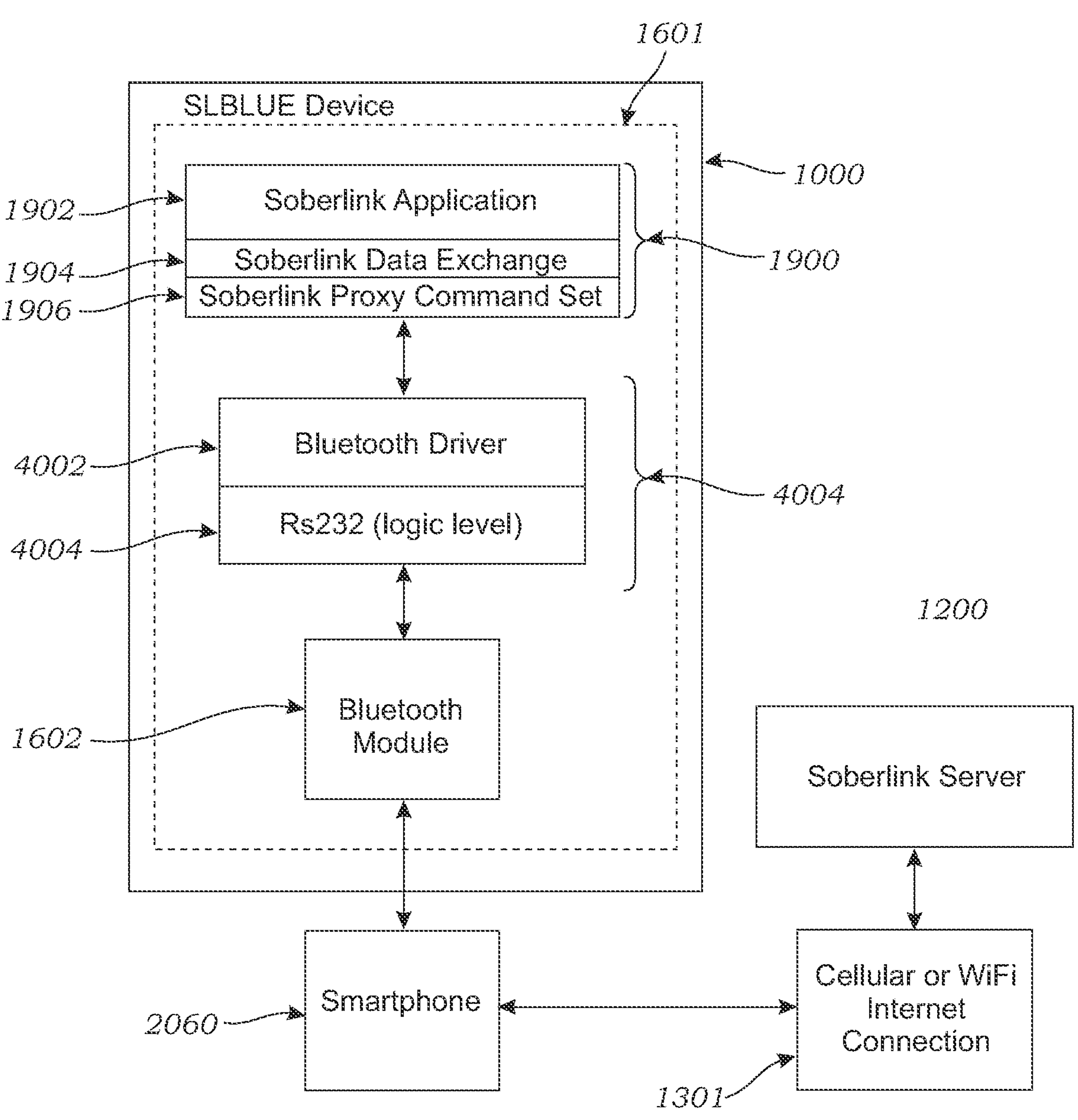
FIG. 6 is a schematic diagram of an example embodiment of a breath testing device utilizing personal-area-network connectivity in accordance with the present invention.

As shown for example in FIG. 6, a breath testing device 1000 may comprise a PAN module 1601 driven by a driver module and communicatively coupled to an intermediary device, such as a smartphone 2060. The intermediary device 2060 is in turn coupled to a monitoring station 1200 or other server 1700 via a wireless network over a cellular and/or Wi-Fi Internet Connection 1301. The PAN module 1601 and driver functionalities described herein may be controlled by a control unit (see e.g. processor 1800 of FIG. 2) executing software instructions retrievably stored in a non-transitory device memory.

In the example embodiment a device application 1902 can be stored in device memory and is associated with a data exchange module 1904 and proxy command set 1906 which combine to form a data module 1900. This data module 1900 can communicate with a Bluetooth driver 4002 and RS232 logic level module 4004 that combine to form a transmission control module 4000. Transmission control module can communicate via Bluetooth module 1602 which can include at least a Bluetooth transceiver 1602 communicating using Bluetooth protocol via connection with a Bluetooth transceiver of smartphone 2060 (not shown).

Additional details of these features and others may be found in U.S. Pat. No. 8,707,758, issued on Apr. 29, 2014; U.S. Pat. No. 8,381,573, issued on Sep. 15, 2010; and U.S. application Ser. No. 13/274,553, filed on Oct. 17, 2011, the entire disclosures and contents of which are herein incorporated by reference in their entirety.

The enablements described in detail above are considered novel over the prior art of record and are considered critical to the operation of at least one aspect of the invention and to the achievement of the above described objectives. The words used in this specification to describe the instant embodiments are to be understood not only in the sense of their commonly defined meanings, but to include by special definition in this specification: structure, material or acts beyond the scope of the commonly defined meanings. Thus, if an element can be understood in the context of this specification as including more than one meaning, then its use must be understood as being generic to all possible meanings supported by the specification and by the word or words describing the element.

The definitions of the words or drawing elements described herein are meant to include not only the combination of elements which are literally set forth, but all equivalent structure, material or acts for performing substantially the same function in substantially the same way to obtain substantially the same result. In this sense it is therefore contemplated that an equivalent substitution of two or more elements may be made for any one of the elements described and its various embodiments or that a single element may be substituted for two or more elements.

Changes from the claimed subject matter as viewed by a person with ordinary skill in the art, now known or later devised, are expressly contemplated as being equivalents within the scope intended and its various embodiments. Therefore, obvious substitutions now or later known to one with ordinary skill in the art are defined to be within the scope of the defined elements. This disclosure is thus meant to be understood to include what is specifically illustrated and described above, what is conceptually equivalent, what can be obviously substituted, and also what incorporates the essential ideas.

Furthermore, the functionalities described herein may be implemented via hardware, software, firmware or any combination thereof, unless expressly indicated otherwise. If implemented in software, the functionalities may be stored as one or more instructions on a computer readable medium, including any available media accessible by a computer that can be used to store desired program code in the form of instructions, data structures or the like. Thus, certain aspects may comprise a computer program product for performing the operations presented herein, such computer program product comprising a computer readable medium having instructions stored thereon, the instructions being executable by one or more processors to perform the operations described herein. It will be appreciated that software or instructions may also be transmitted over a transmission medium as is known in the art. Further, modules and/or other appropriate means for performing the operations described herein may be utilized in implementing the functionalities described herein.

The scope of this description is to be interpreted only in conjunction with the appended claims and it is made clear, here, that the named inventor believes that the claimed subject matter is what is intended to be patented.

What is claimed is:

1. A sample pump comprising:

an inlet port configured to draw an air sample into the sample pump;

a bellows assembly configured to expand and compress;

a trigger assembly comprising a wire trigger structure and a bi-stable trigger spring, wherein the trigger structure is configured to transform into a predetermined shape in response to a first current being applied to the trigger structure, wherein the trigger structure, upon transforming into its predetermined shape, is configured to exert a force on the bi-stable trigger spring and cause the bellows assembly to expand; and a retraction assembly comprising a first wire element and a second wire element, wherein the first wire element and the second wire element are composed of a first shape memory alloy, wherein the first wire element and the second wire element are configured to compress in response to a second current and cause the bellows assembly to compress.

2. The sample pump of claim 1, wherein the trigger assembly is housed within an interior of the bellows assembly.

3. The sample pump of claim 1, wherein the trigger structure is composed of a second shape memory alloy.

4. The sample pump of claim 3, wherein the second shape memory alloy comprises nitinol.

5. The sample pump of claim 1, wherein the first shape memory alloy comprises nitinol.

6. The sample pump of claim 1, wherein the bi-stable trigger spring is configured to transition between a pre-triggered position and a post-triggered position in response to the force exerted on the bi-stable trigger spring by the trigger structure.

7. The sample pump of claim 6, wherein the bi-stable trigger spring is further configured to exert a force on an interior wall of the bellows assembly when in the post-triggered position.

8. The sample pump of claim 7, wherein the bellows assembly is further configured to expand in response to the bi-stable spring exerting the force on the interior wall.

9. The sample pump of claim 6, wherein in the pre-triggered position, the bi-stable trigger spring comprises an arch having a convex portion with an apex pointing downwardly towards the trigger structure.

10. The sample pump of claim 9, wherein the post-triggered position, the arch is configured to invert and comprise a concave portion with the apex pointing upwardly toward an upper interior wall of the bellows assembly.

11. The sample pump of claim 6, the bi-stable trigger spring is further configured to transition between the pre-triggered position and the post-triggered position in response to the trigger structure transforming into the predetermined shape.

12. The sample pump of claim 6, wherein the bi-stable trigger spring is in the post-triggered position after the first current is applied and after a predetermined temperature has been exceeded, wherein the predetermined temperature is a temperature at which the trigger structure transforms into the predetermined shape in response.

13. The sample pump of claim 1, wherein the retraction assembly is configured along an exterior surface of the sample pump.

14. The sample pump of claim 1, wherein the retraction assembly further comprises a holding structure configured along a top surface of the sample pump, wherein the holding structure is further configured to support the first wire element and the second wire element.

15. The sample pump of claim 14, wherein the holding structure is further configured to push down and compress the bellows assembly in response to the first wire element and the second wire element compressing.

16. The sample pump of claim 1, further comprising a rigid frame configured to provide structural support for the bellows assembly, wherein the rigid frame is positioned along an inner perimeter of the bellows assembly, and wherein the bellows assembly is positioned outside the rigid frame.

17. The sample pump of claim 16, wherein the bi-stable trigger spring is configured to extend upwardly from an upper surface of the rigid frame.

18. The sample pump of claim 1, wherein the bi-stable trigger spring is operatively coupled with the trigger structure, and wherein at least a portion of the bi-stable trigger spring is configured to at least partially overlay the trigger structure.

19. The sample pump of claim 1, wherein the first current and the second current are applied via a battery.

20. The sample pump of claim 1, further comprising a reflective surface configured to allow a sensor to measure a distance traveled by the bellows assembly when the bellows assembly expands.

* * * * *